United States Patent

Massonne et al.

[11] Patent Number: 6,020,501
[45] Date of Patent: Feb. 1, 2000

[54] PROCESS FOR PREPARING PHTHALIDES

[75] Inventors: Klemens Massonne, Westheim; Rainer Becker, Bad Dürkheim; Wolfgang Reif; Joachim Wulff-Döring, both of Frankenthal, all of Germany

[73] Assignee: BASF Aktiengesellschaft, Ludwigshafen, Germany

[21] Appl. No.: 09/214,512

[22] PCT Filed: Jun. 24, 1997

[86] PCT No.: PCT/EP97/03303

§ 371 Date: Jan. 7, 1999

§ 102(e) Date: Jan. 7, 1999

[87] PCT Pub. No.: WO98/01438

PCT Pub. Date: Jan. 15, 1998

[30] Foreign Application Priority Data

Jul. 10, 1996 [DE] Germany .............. 196 27 697

[51] Int. Cl.[7] .................................................. C07D 307/83
[52] U.S. Cl. ...................... 549/307; 549/305; 549/310
[58] Field of Search ....................... 549/307, 310

[56] References Cited

U.S. PATENT DOCUMENTS

| | | | |
|---|---|---|---|
| 3,957,825 | 5/1976 | Urry et al. | 260/343 |
| 3,997,478 | 12/1976 | Petro | 252/470 |
| 4,485,246 | 11/1984 | Lyons | 549/302 |
| 4,528,385 | 7/1985 | Fuenten et al. | 549/307 |
| 5,296,614 | 3/1994 | Henkelmann et al. | 549/307 |

FOREIGN PATENT DOCUMENTS

| | | |
|---|---|---|
| 089417 | 9/1983 | European Pat. Off. . |
| 542037 | 5/1993 | European Pat. Off. . |
| 2803319 | 8/1979 | Germany . |

OTHER PUBLICATIONS

Houben–Weyl, *Methoden der organischen Chemie,* Jun. 2, 1963, pp. 732–733 (translation).

*Primary Examiner*—Amelia Owens
*Attorney, Agent, or Firm*—Keil & Weinkauf

[57] ABSTRACT

The disclosure is a process for preparing a phthalide of the general formula I

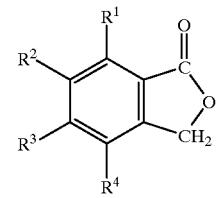

I where $R^1$, $R^2$, $R^3$ and $R^4$ are each independently of the others hydrogen, $C_1$–$C_4$-alkyl or $C_1$–$C_4$-alkoxy, by hydrogenation of a phthalic anhydride of the general formula II

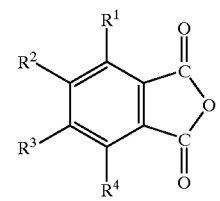

II where $R^1$, $R^2$, $R^3$ and $R^4$ are each as defined above, with the aid of a hydrogenation catalyst, which comprises performing the hydrogenation with the aid of a nickel catalyst doped with metals of subgroup 1, subgroup 6 and/or subgroup 7 of the Periodic Table.

4 Claims, No Drawings

PROCESS FOR PREPARING PHTHALIDES

DESCRIPTION

The present invention relates to a process for preparing phthalides by catalytic hydrogenation of phthalic anhydrides with the aid of nickel catalysts doped with metals of subgroup Ib, subgroup VIb and/or subgroup VIIB of the Periodic Table.

DE-C-28 03 319 discloses a process for preparing phthalide by catalytic hydrogenation of phthalic anhydride in the gas phase using copper- and aluminum-containing catalysts. However, this process is prohibitively costly at the product isolation stage, involving as it does multistage condensation and a downstream waste gas scrub. EP-A-542 037 describes a process for preparing phthalides by catalytic hydrogenation of phthalic anhydride over fixed bed catalysts. This process needs large quantities of catatlyst and long hydrogenation times when practiced batchwise and high pressures to achieve complete conversion when practiced continuously.

U.S. Pat. Nos. 4,485,246 and 3,957,825 disclose that it is possible to prepare phthalide from phthalic anhydride by hydrogenation with homogeneous ruthenium catalysts. Catalyst recovery is difficult in these processes.

EP-B-89 417 describes the catalytic hydrogenation of phthalic anhydride to phthalide with the aid of a nickel catalyst immobilized on a support material using methyl benzoate as mandatory solvent. The process has the disadvantage of high catalyst requirements and long reaction times.

It is further known from Houben/Weyl, Methoden der organischen Chemie, 6/2 (1963), 732 to 733, to hydrogenate phthalic anhydride to phthalide with the aid of Raney nickel as catalyst, but a hydrogen pressure of 165 bar and ethanol as solvent affords a phthalide yield of only 73%.

It is an object of the present invention to remedy the aforementioned disadvantages of using existing catalysts in the catalytic hydrogenation of phthalic anhydrides.

We have found that this object is achieved by a novel and improved process for preparing a phthalide of the general formula I

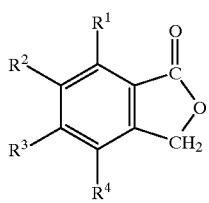

I where $R^1$, $R^2$, $R^3$ and $R^4$ are each independently of the others hydrogen, $C_1$–$C_4$-alkyl or $C_1$–$C_4$-alkoxy, by hydrogenation of a phthalic anhydride of the general formula II

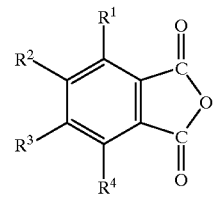

II where $R^1$, $R^2$, $R^3$ and $R^4$ are each as defined above, with the aid of a hydrogenation catalyst, which comprises performing the hydrogenation with the aid of a nickel catalyst doped with metals of subgroup 1, subgroup 6 and/or subgroup 7 of the Periodic Table.

The process of the invention makes it possible to perform the hydrogenation of phthalic anhydrides to phthalides at low levels of catalyst, with a good space-time yield and in high selectivity. The catalysts to be used according to the invention have distinctly increased activity compared with conventional Raney nickel. This leads to milder reaction conditions or, under the customary reaction conditions for undoped Raney nickel, to faster hydrogenation and hence to higher space-time yields.

Compared with the catalysts to be used in the process described in EP-A-542 037, the catalysts to be used according to the invention likewise have distinctly increased activity. Whereas the known process generally produces only incomplete conversions after 12 hours' hydrogenation and 260 bar pressure using 10% of catalyst, based on the phthalic anhydride used, despite the use of high reaction temperatures of from 150 to 250° C., the process of the invention affords virtually complete conversion under milder reaction conditions and in a shorter time.

The catalytic hydrogenation is generally carried out at temperatures from 50 to 400° C., preferably from 100 to 250° C., especially from 140 to 220° C., and pressures from 1 to 400 bar, preferably from 5 to 300 bar, especially from 5 to 200 bar, particularly advantageously from 30 to 120 bar.

Customary hydrogenation reactors can be used, for example autoclaves or tubular reactors.

The hydrogenation catalysts used for the process of the invention are nickel catalysts doped with metals of subgroup Ib of the Periodic Table, generally silver, copper, preferably copper, with metals of subgroup VIb of the Periodic Table, generally chromium, molybdenum or tungsten, preferably molybdenum, and/or with metals of group VIIb of the Periodic Table, generally manganese, rhenium, preferably rhenium. In general, the level of doping metals in the catalysts to be used according to the invention ranges from 0.01 to 10% by weight, preferably from 0.1 to 5% by weight, based on the nickel present in the catalysts.

The catalysts to be used according to the invention are prepared in a conventional manner (DE-A-25 44 761), for example by alloying nickel, the doping metals and alkali-leachable substances, preferably aluminum and/or silicon, and then leaching out the alkali-soluble substances using an alkali, such as aqueous sodium solution.

Preferred nickel catalysts are doped Raney nickel catalysts. The hydrogenation catalysts can be used for example as supported catalysts or suspended catalysts.

The hydrogenation can be carried out without solvent, in which case the phthalic anhydride is used in molten form.

In general, the hydrogenation is carried out using a solvent. Examples of suitable solvents are ethers such as tetrahydrofuran, dioxane, glycol ethers, esters such as methyl acetate and methyl benzoate, lactones such as butyrolactone or phthalide, preferably the phthalide formed in the course of the hydrogenation, alcohols such as methanol, ethanol, propanol, butanol, hydrocarbons or mixtures thereof.

The weight ratio of phthalic anhydride to be hydrogenated to the solvent used is generally within the range from 1000:1 to 1:1000, preferably within the range from 500:1 to 1:500, especially within the range from 200:1 to 1:200.

The reaction of the invention is advantageously discontinued as soon as all the phthalic anhydride used has been hydrogenated. The time for discontinuation is determined for example by determining the phthalic anhydride still present, for example by gas chromatography or from the time course of hydrogen consumption.

The reaction product is worked up in a conventional manner, preferably by distillation.

In the compounds I and II, $R^1$, $R^2$, $R^3$ and $R^4$ are each independently of the others hydrogen; $C_1$–$C_4$-alkyl such as methyl, ethyl, n-propyl, isopropyl, n-butyl, isobutyl, sec-butyl, tert-butyl, preferably methyl and ethyl, especially methyl; $C_1$–$C_4$-alkoxy such as methoxy, ethoxy, n-propoxy, isopropoxy, n-butoxy, isobutoxy, sec-butoxy, tert-butoxy, preferably methoxy and ethoxy, especially methoxy. $R^1$, $R^2$, $R^3$ and $R^4$ are particularly preferably all hydrogen.

The phthalic anhydrides II used as starting materials are well known, such as phthalic anhydride itself, or can be obtained by known processes (J. of Org. Chemistry 51, 3439–3446 (1986); Synthesis 223–224 (1985)).

The phthalides I are used for example as starting materials for the synthesis of crop protection agents.

The Examples which follow illustrate the invention.

INVENTIVE EXAMPLE 1

A 0.5 l stirred autoclave equipped with a sparging stirrer is charged with 88.8 g of phthalic anhydride, 207.2 g of phthalide as solvent and 0.9 g of catalyst under nitrogen, and the phthalic anhydride/phthalide mixture is melted at 120° C. The stirrer is switched on with a speed 500 rpm, and the nitrogen is exchanged for hydrogen by repeated injection of hydrogen to a pressure of 5 bar and decompression. The reactor contents are heated to 180° C. Hydrogen is injected to a pressure of 40 bar, and the hydrogenation is continued to constant pressure. The conversion of phthalic anhydride is then virtually quantitative.

The experimental conditions and results are summarized in the following table:

| Run No. | Catalyst | Doping in % by weight based on nickel content of catalyst | Hydrogenation time min | Selectivity % |
|---|---|---|---|---|
| 1a | Raney nickel (catalyst BK 113 W; Degussa) | 1% of molybdenum | 115 | 87 |
| 1b | Raney nickel (catalyst BK 111 W; Degussa) | 1% of molybdenum | 79 | 89 |
| 1c | Raney nickel (catalyst Actimet C; Doduco) | 1% of molybdenum | 103 | 89 |
| 1d | Raney nickel | 1% of copper | 70 | 86 |
| 1e | Raney nickel | 1% of rhenium | 30 | 88 |

Comparative Examples

The runs of Inventive Example 1 are repeated using undoped Raney nickel catalysts and Raney nickel catalysts not doped in accordance with the invention.

The experimental conditions and results are summarized in the following table:

| Run No. | Catalyst | Doping | Hydrogenation time min | Selectivity % |
|---|---|---|---|---|
| 2a | Raney nickel (B 113 CW; Degussa) | none | 208 | 85 |
| 2b | Raney nickel (B 113 Z; Degussa) | none | 203 | 84 |
| 2c | Raney nickel (Actimet S; Doduco) | none | 177 | 80 |
| 2d | Raney nickel (Actimet MA; Doduco) | none | 145 | 86 |
| 2e | Raney nickel (BM 113 Z; Degussa) | 1% of iron | 338 | 87 |

The Raney nickel catalysts which are not in accordance with the invention need distinctly longer hydrogenation times to achieve a comparable conversion, and the selectivity is lower too, in general.

We claim:
1. A process for preparing a phthalide of the formula I

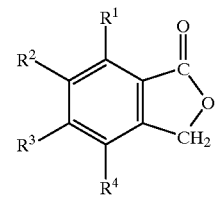

where $R^1$, $R^2$, $R^3$ and $R^4$ are each independently of the others hydrogen, $C_1$–$C_4$-alkyl or $C_1$–$C_4$-alkoxy, by hydrogenation of a phthalic anhydride of the general formula II

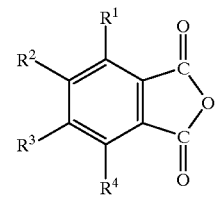

where $R^1$, $R^2$, $R^3$ and $R^4$ are each as defined above, with the aid of a hydrogenation catalyst, which comprises performing the hydrogenation with the aid of a Raney nickel catalyst doped with metals of subgroup Ib, subgroup VIb and/or subgroup VIIb of the Periodic Table.

2. The process of claim 1 wherein the dopant is copper.

3. The process of claim 1, wherein the dopant is molybdenum.

4. The process of claim 1, wherein the dopant is rhenium.

* * * * *